United States Patent
Bäckström

(10) Patent No.: US 11,026,954 B2
(45) Date of Patent: Jun. 8, 2021

(54) 3-BETA-HYDROXY-5-ALPHA-PREGNAN-20-ONE FOR USE IN MEDICAL TREATMENT

(71) Applicant: ASARINA PHARMA AB, Solna (SE)

(72) Inventor: Torbjörn Bäckström, Umeå (SE)

(73) Assignee: ASARINA PHARMA AB, Solna (SE)

( * ) Notice: Subject to any disclaimer, the term of this patent is extended or adjusted under 35 U.S.C. 154(b) by 0 days.

(21) Appl. No.: 16/484,940

(22) PCT Filed: Sep. 2, 2018

(86) PCT No.: PCT/SE2018/050119
§ 371 (c)(1),
(2) Date: Aug. 9, 2019

(87) PCT Pub. No.: WO2018/147792
PCT Pub. Date: Aug. 16, 2018

(65) Prior Publication Data
US 2019/0358245 A1    Nov. 28, 2019

(30) Foreign Application Priority Data

Feb. 10, 2017 (SE) .................................. 1750125-5
Oct. 3, 2017 (SE) .................................. 1751222-9

(51) Int. Cl.
*A61K 31/56* (2006.01)
*A61K 31/36* (2006.01)
(Continued)

(52) U.S. Cl.
CPC .......... *A61K 31/573* (2013.01); *A61K 31/136* (2013.01); *A61K 31/138* (2013.01);
(Continued)

(58) Field of Classification Search
CPC ...................................................... A61K 31/57
(Continued)

(56) References Cited

U.S. PATENT DOCUMENTS 5,232,917 A    8/1993 Bolger et al.
5,939,545 A    8/1999 Upasani et al.
(Continued)

FOREIGN PATENT DOCUMENTS

EP    2875810 A1    5/2015
WO    WO99/36064 A2    7/1999
(Continued)

OTHER PUBLICATIONS

Umathe et al. "Neurosteroids modulate compulsive and persistent behavior in rodents: implications of obsessive-compulsive disorder," Progress in Neuro-Psychopharmacology & Biological Psychiatry, 2009, vol. 33, pp. 1161-1166 (Year: 2009).*
(Continued)

*Primary Examiner* — Shengjun Wang
(74) *Attorney, Agent, or Firm* — Cermak Nakajima & McGowan LLP; Malcolm K. McGowan

(57) ABSTRACT

The present invention provides the steroid compound 3beta-hydroxy-5alpha-pregnan-20-one for use in treatment of Tourette's syndrome, obsessive compulsive disorder and/or gambling disorder, as well as methods for treating said disorders and pharmaceutical compositions for use in treatment of said disorders.

14 Claims, 3 Drawing Sheets

(51) Int. Cl.

| | | |
|---|---|---|
| A61K 31/44 | (2006.01) | |
| A61K 31/519 | (2006.01) | |
| A61K 31/504 | (2006.01) | |
| A61K 31/415 | (2006.01) | |
| A61K 31/165 | (2006.01) | |
| A61K 31/55 | (2006.01) | |
| A61K 31/573 | (2006.01) | |
| A61K 31/136 | (2006.01) | |
| A61K 31/138 | (2006.01) | |
| A61K 31/15 | (2006.01) | |
| A61K 31/155 | (2006.01) | |
| A61K 31/343 | (2006.01) | |
| A61K 31/4168 | (2006.01) | |
| A61K 31/451 | (2006.01) | |
| A61K 31/454 | (2006.01) | |
| A61K 31/496 | (2006.01) | |
| A61K 31/5415 | (2006.01) | |
| A61K 31/58 | (2006.01) | |

(52) U.S. Cl.
CPC ............ *A61K 31/15* (2013.01); *A61K 31/155* (2013.01); *A61K 31/343* (2013.01); *A61K 31/4168* (2013.01); *A61K 31/451* (2013.01); *A61K 31/454* (2013.01); *A61K 31/496* (2013.01); *A61K 31/519* (2013.01); *A61K 31/5415* (2013.01); *A61K 31/55* (2013.01); *A61K 31/58* (2013.01)

(58) Field of Classification Search
USPC ........................................................ 514/182
See application file for complete search history.

(56) References Cited

U.S. PATENT DOCUMENTS

| | | | |
|---|---|---|---|
| 6,455,516 B1 | 9/2002 | Backström et al. | |
| 2004/0048876 A1 | 3/2004 | Busch et al. | |
| 2005/0256029 A1 | 11/2005 | Murphy et al. | |
| 2011/0184012 A1* | 7/2011 | Murphy .................. | A61P 25/00 514/300 |
| 2017/0020952 A1 | 1/2017 | Hruby et al. | |

FOREIGN PATENT DOCUMENTS

| | | |
|---|---|---|
| WO | WO99/45931 A1 | 9/1999 |
| WO | WO01/08670 A2 | 2/2001 |
| WO | WO03/059357 A1 | 7/2003 |
| WO | WO2008/063128 A1 | 5/2008 |
| WO | WO2011/087441 A1 | 7/2011 |
| WO | WO2016/040322 A1 | 3/2016 |
| WO | WO2016/114655 A1 | 7/2016 |
| WO | WO2016/164763 A1 | 10/2016 |
| WO | WO2016/209929 A1 | 12/2016 |
| WO | WO2016/209929 A8 | 12/2016 |

OTHER PUBLICATIONS

Sandor, P., "Pharmacological management of tics in patents with TS," J. Psychoshomatic Res. 2003;55:41-48.

Umathe, S. N. et al., "Neurosteroids modulate compulsive and persistent behaviour in rodents: Implications for obsessive-compulsive disorder," Progress in Neuro-Psychopharmacology & Biological Psychiatry 2009;33:1161-1166.

Wang, M.D., et al., "The inhibitory effects of allopregnanolone PC and pregnanolone on the population spike, evoked in the rat hippocampal CA1 stratum pyramidale in vitro, can be blocked selectively by epiallopregnanolone," Acta. Physiol. Scand. 2000;169:333-341.

Wang, M., et al., "3beta-Hydroxypregnane Steroids Are Pregnolone Sulfate-Like GABAA Receptor Antagonists," J Neurosci. 2002;22(9):3366-3375.

Nordstrom, E. J., et al., "A transgenic model of comorbid Tourette's syndrome and obsessive-compulsive disorder circuitry," Mol. Psychiatry 2002;7:617-625.

International Search Report for PCT Patent App. No. PCT/SE2018/050119 (dated Apr. 16, 2018).

Prince, R. J., et al., "Differential antagonism by epipregnanolone of alphaxalone and pregnanolone potentiation of [3H]flunitrazepam binding suggests more than one class of binding site for steroids at GABAA receptors" Neuropharmacology, (1993);32:59-63.

* cited by examiner

3-BETA-HYDROXY-5-ALPHA-PREGNAN-20-ONE FOR USE IN MEDICAL TREATMENT

CROSS-REFERENCE TO RELATED APPLICATIONS

This application is a National Stage Entry of PCT/SE2018/050119, filed Feb. 9, 2018, which claims priority from Swedish patent applications 1750125-5, filed Feb. 10, 2017, and 1751222-9, filed Oct. 3, 2017. The contents of these priority applications are incorporated herein by reference in their entirety.

FIELD OF THE INVENTION

The present invention provides the steroid compound 3beta-hydroxy-5alpha-pregnan-20-one for use in treatment of Tourette's syndrome, obsessive compulsive disorder and/or gambling disorder, as well as methods for treating said disorders and pharmaceutical compositions for use in treatment of said disorders.

BACKGROUND OF THE INVENTION

Tourette's syndrome or Tourette syndrome (TS) is a neurodevelopmental disorder characterized by recurring motor and phonic tics with multiple involuntary movements (motor tics) and one or more vocal (phonic) tics. It affects up to one percent of children worldwide, of whom about one third continue to experience symptoms into adulthood. The pathogenesis of TS is thought to reflect dysregulations in the signaling of neurotransmitters, among them y-amino-butyric acid (GABA), dopamine and glutamate, which lead to excitation/inhibition imbalances in cortico-striato-thalamo-cortical circuits (CST). $GABA_A$ pathways are interacting with dopamine signaling in several layers of the CST and as both dopamine and GABA are inhibitory, this may cause a disinhibition that is thought to be the pathogenesis of TS. Dopamine is known to release GABA in striatum. The causes of these deficits reflect complex gene×environment×sex interactions. The $GABA_A$ receptor subtype highly expressed in thalamus is the alpha4,beta,delta subtype. This subtype is known to be highly sensitive to $GABA_A$ receptor modulating steroids e.g. allopregnanolone. The disorder is more prevalent in males, with a ratio of 4:1. Evidence suggests that tics are the phenotypic correlate of the activation of ectopic foci in the basal ganglia, due to excitation/inhibition imbalances in CST connections. Notably is that exposure to psychosocial stress with high production stress steroids has been highlighted as key enhancer of symptoms in TS pathogenesis, indicating involvement of stress related neuroactive steroids. Especially androgen metabolites, androstanes, and progesterone metabolites, pregnanes present both in men and women are clinically observed to exacerbated tics in TS patients.

Obsessive compulsive disorder (OCD) is a psychiatric disorder where people feel the need to check things repeatedly, perform certain "rituals", or have certain thoughts repeatedly. People with OCD are unable to control either their thoughts or their activities for more than a short period of time. Common activities include hand washing, counting of things, and checking to see if a door is locked. The activities occur so often that the person's daily life is influenced negatively. Most adults realize that the behaviors do not make sense. The condition is associated with tics, anxiety disorder, and an increased risk of suicide. OCD involves genetic components. Risk factors include stress inducing events, a history of child abuse or infectious disease.

Treatment involves counseling, such as cognitive behavioral therapy (CBT), and sometimes medication, typically selective serotonin reuptake inhibitors (SSRIs). However, symptoms may persist at moderate levels even following adequate treatment courses, and completely symptom-free periods are uncommon. Without treatment, the condition often lasts for decades. OCD rates during a given year are approximately 1.2% and the disease occurs worldwide. OCD affects approximately 2.3% of people at some point in their life. Half of the people develop symptoms before the age of twenty, men and women are affected about equally.

Functional neuroimaging studies have led to a greater understanding of the neurobiology of OCD, providing strong evidence that the pathophysiology of OCD involves abnormal functioning along specific, fronto-subcortical brain circuits. A currently accepted theory about etiological mechanism of OCD claims that the dysfunctions that exist in the Cortico-Striato-Thalamo-Cortical circuit (CST), especially in Orbitofrontal Cortex (OFC), Anterior Cingulate Cortex (ACC), striatum, thalamus and other parts of the circuit, are crucial for the pathogenesis of OCD. The $GABA_A$ receptor subtype highly expressed in thalamus is the alpha4,beta,delta subtype. This subtype is known to be highly sensitive to $GABA_A$ receptor modulating steroids e.g. allopregnanolone. The symptoms are thought to reflect dysregulations in the signaling of neurotransmitters, among them y-amino-butyric acid (GABA), dopamine and glutamate, which lead to excitation/inhibition imbalances in cortico-striato-thalamo-cortical circuits (CST). $GABA_A$ pathways are interacting with dopamine signaling in several layers of the CST and as both dopamine and GABA are inhibitory, this may cause a disinhibition that is thought to be the pathogenesis. GABA-A receptor modulating steroids are reported to modulate GABAergic pathways that then influence serotonin and dopamine, the neurotransmitters implicated in pathophysiology of OCD. Studies indicate that neurosteroids can modulate obsessive-compulsive behaviour in a bidirectional manner, and could serve as an effective target in the management of OCD.

Gambling disorder (GD) (previously termed Pathological gambling) is a disorder similar to OCD but also shares similarities with abuse disorders 'substance-related and addictive disorders' in DSM-5. Gambling Disorder, Problem gambling, gambling addiction or compulsive gambling is an urge to gamble continuously despite harmful negative consequences or a desire to stop. Problem gambling is often defined by whether harm is experienced by the gambler or others, rather than by the gambler's behavior. Severe problem gambling may be diagnosed as clinical gambling disorder if the gambler meets certain criteria. Gambling disorder is a common disorder that is associated with both social and family costs. The DSM-5 has re-classified the condition as an addictive disorder, with sufferers exhibiting many similarities to those who have substance addictions. The term "gambling addiction" has long been used in the recovery movement. Pathological gambling was long considered by the American Psychiatric Association to be an impulse control disorder rather than an addiction. The DSM-5 has since reclassified pathological gambling as "gambling disorder" and has listed the disorder under substance-related and addictive disorders rather than impulse-control disorders. This is due to the symptomatology of the disorder resembling an addiction. There are both environmental and genetic factors that can influence the gambler and cause some type of addiction. However, no specific treatment is considered to be most efficacious and no medications have been approved for the treatment of gambling disorder by the U.S. Food and Drug Administration (FDA). In the United States, the percentage of pathological gamblers was 0.6 percent, and the percentage of problem gamblers was 2.3 percent in 2008.

Impulsivity is an established precursor to addictive behaviors, and GD is associated with greater impulsivity. There is also evidence of GABAergic dysregulation in addiction and impulsivity. The $GABA_A$ receptor availability in GD compared to healthy volunteers (HV) show significantly higher $GABA_A$ receptor availability in the right hippocampus of GD individuals compared with HV. There is a positive association of "Urgency impulsivity" in GD, and $GABA_A$ receptor availability in the amygdala in a GD group but not in a control group. These results indicate a GABAergic dysregulation in gambling disorders and is a potential target for treatment.

As the main inhibitory neurotransmitter in the human brain, the role of GABAergic functioning in impulsivity, is attracting attention with growing preclinical evidence supporting its involvement. For instance, a GABA agonist and antagonist in the prefrontal cortex of rats increased and reduced, respectively, impulsive responses in a reaction time task. Greater $GABA_A$ receptor availability, which may be due to increased $GABA_A$ receptor expression, is found in the hippocampus of individuals with GD. In addition, the $GABA_A$ receptor binding capacity is positively related to impulsivity. Evidence from pharmacological challenges with GABA modulating drugs such as benzodiazepines suggests that increased GABAergic neurotransmission is associated with impulsivity. A positive modulator of the $GABA_A$ receptor, allopregnanolone, has been shown to increase risk taking and aggressive behavior in rodents of both sexes.

$GABA_A$ receptor modulating steroids are metabolites of the sex and stress hormones pregnenolone, progesterone, deoxycorticosterone, cortisone and cortisol, known as pregnanolones; as well as the metabolites of testosterone, androstandione and dehydroepiandrosterone, known as androstanes, have all been the subject of various studies, at least partially elucidating their role in the neurological signal system in mammals. The harmful steroids inducing CNS symptoms and disorders of interest in the present application all have a structural similarity in comprising a 3alpha-hydroxy group, a Δ4-pregnene or a 5alpha or 5beta pregnane steroid body, and a ketone or hydroxy group on position 17, 20 or 21.

Steroids comprising 3alpha-hydroxy-5alpha/beta-pregnan/Δ4-pregnen-20-one/ol or 3alpha-hydroxy-5alpha/beta-androstan/Δ4-androsten-17-one/ol have been shown to be important specific enhancers of the $GABA_A$ receptor. They bind to the $GABA_A$ receptor and act by enhancing the effect of GABA in terms of prolonging the $GABA_A$ receptors opening duration. The receptors are of several subtypes located to different areas of the brain and related to different CNS disorders and symptoms. In addition some receptors are localized within a synapse (intra-synaptic) while others are located outside a synapse (extra-synaptic). $GABA_A$ receptor modulating steroids can by themselves in physiological concentrations open the extra-synaptic $GABA_A$ receptor alone (tonic inhibition) but not the intra-synaptic receptors (phasic inhibition). These two types of effects are dependent on different mechanisms and binding sites on the $GABA_A$ receptor and the effects depends in addition on the subunit composition of the receptor. The receptor subtype alpha4,beta,delta is an extra-synaptic subtype with both tonic and phasic effects of 3alpha-hydroxy-5alpha/beta-pregnan-20-one/ol and 3alpha-hydroxy-5alpha/beta-androstan-17-one/ol. No specific $GABA_A$ modulating steroid antagonists acting on both binding sites or only inhibits one of the mechanisms are known today among persons skilled in the art. The effect of 3alpha-hydroxy-5alpha/beta-pregnan-20-one/ol or 3alpha-hydroxy-5alpha/beta-androstan-17-one/ol is similar to the effects of both benzodiazepines and barbiturates, i.e. they are all positive modulators of the $GABA_A$ receptor. Said steroid compounds, however, have a binding site separate from that of both these compounds.

The severity of behavioral symptoms in TS, OCD and GD is exacerbated by psychosocial stress. Clinical observations have shown that tics in TS patients are exacerbated by anabolic androgens. In women tics increase during the luteal phase when $GABA_A$ receptor modulating pregnane-steroids are high. Treatment with the hormonal androgen receptor blocker flutamide resulted in a very modest (7%), amelioration of motor tic severity but no significant effects were observed on phonic tics suggesting that the hormonal effect via the hormonal receptor was of minor importance. This suggests that the effect by stress and sex steroids (pregnanes and androstanes) is not mediated via the classical hormonal receptors. Stress and sex steroid hormones are metabolized to form 3alpha-hydroxy-5alpha/beta-steroids that are positive modulators of the $GABA_A$ receptor. The synthesis of 3alpha-hydroxy-5alpha/beta-steroids occurs in the brain and one key rate-limiting enzyme catalyzing the synthesis of 3alpha-hydroxy-5alpha-pregnane and androstane neurosteroids is the 5alpha-reductase. If the 5alpha-reductase enzyme is blocked the 3alpha-hydroxy-5alpha-pregnane and androstane neurosteroids are not formed. Preliminary studies using the 5alpha-reductase blocker finasteride showed a reduction of ticks over a period of 12-18 weeks.

Prince and Simmons (Neuropharmacology, vol. 32, no. 1, pp. 59-63, 1993) have used a model relying on membrane fractions of whole male rat brain. In this sub-fraction of whole brain homogenate, the authors used the binding of a benzodiazepine, $^3$H-flunitrazepam, as a model for steroid effect and change of $GABA_A$ receptor conformation. This test has been suggested to be an indicator of allosteric modulation of the $GABA_A$ receptor. This is a very general analysis method and does not take into account specificity depending on subunit composition, intra or extra-synaptic effects or different $GABA_A$ modulating steroids. The relationship between the change in flunitrazepam (FNZ) binding and change in chloride flow at GABA stimulation is however uncertain and a change in binding cannot be taken as a proof of a change in the chloride flow through the GABA receptor, nor as a proof of a change in $GABA_A$ receptor function. The existence of a relationship between change in FNZ-binding and neuronal excitability, is even less clear and such conclusions cannot be drawn from results on FNZ-binding alone. A change in FNZ-binding properties or absence of such change in binding properties does not imply a change or the absence of a change in neural activity or $GABA_A$ mediated chloride flow.

It is also known that the $GABA_A$ receptor contains several sub-units that can be combined in multiple ways. Interestingly, certain combinations lack steroid recognition site. It is also known that the effect of steroid on the binding of a convulsant substance TBPS (t-butylbicyclo-phosphorothionate) differs in different brain regions. Further, it is known that the binding of TBPS varies with the oestrus cycle in female rats indicating an effect change related to sex steroid hormone production.

U.S. Pat. Nos. 5,232,917 and 5,939,545 disclose a number of 3alpha-hydroxy steroids. These disclosures concern the agonistic modulation of the $GABA_A$ receptor. In other words, the disclosures are both focused on the benzodiazepine-like effect of the 3alpha-hydroxy-5alpha/beta-steroids. All steroids that are positive modulators of the $GABA_A$ receptor have the common feature of a 3alpha-hydroxy structure. Steroids with only a 3beta-hydroxy structure have never been shown to possess a $GABA_A$ receptor positive modulating effect. In all cases where an effective $GABA_A$ receptor-modulating effect is noticed, the steroid has a 3alpha-hydroxy group.

WO 99/45931 discloses a $GABA_A$ modulating steroid antagonist, namely 3beta-hydroxy-5alpha-pregnan-20-one but does not mention the effect in different receptor subtype e.g. the alpha4,beta,delta subtype and does not describe 3beta-hydroxy-5alpha-pregnan-20-one effects on phasic or tonic 3alpha-hydroxy-5alpha/beta-steroid activity in intra- or extra-synaptic receptors.

The $GABA_A$ modulating steroid antagonist effect of 3beta-hydroxy-5alpha-pregnan-20-one against 3alpha-hydroxy-5alpha/beta-pregnan-20-one was first disclosed by Wang et al. (Wang M. D., Bäckström T. and Landgren S. (2000) Acta Physiol Scand 169, 333-341). In that disclosure, a dose dependent antagonistic effect of 3beta-hydroxy-5alpha-pregnan-20-one on two of the 3alpha-hydroxy-5alpha/beta-steroids was shown. This document does not mention the possibility to use 3beta-hydroxy-5alpha-pregnan-20-one against disorders caused by androgenic $GABA_A$ receptor modulating steroids and the possibility to use 3beta-hydroxy-5alpha-pregnan-20-one as inhibitor at the alpha4,beta,delta activated $GABA_A$ receptor and does not disclose 3beta-hydroxy-5alpha-pregnan-20-one effects on phasic or tonic 3alpha-hydroxy-5alpha/beta-steroid activity in intra- or extra-synaptic receptors.

WO 03/059357 discloses the use of certain pregnane steroids in the treatment of CNS disorders. This document does not mention the possibility to use 3beta-hydroxy-5alpha-pregnan-20-one against disorders caused by androgenic $GABA_A$ receptor modulating steroids and the possibility to use 3beta-hydroxy-5alpha-pregnan-20-one as inhibitor at the alpha4,beta,delta activated $GABA_A$ receptor and does not disclose 3beta-hydroxy-5alpha-pregnan-20-one effects on phasic or tonic 3alpha-hydroxy-5alpha/beta-steroid activity in intra- or extra-synaptic receptors.

3beta steroids can also have effects on the GABA's own effect as disclosed by Wang et al. (The Journal of Neuroscience, May 1, 2002, 22(9):3366-3375). In this disclosure, the authors show that when maximal stimulation of $GABA_A$ receptors is made with GABA, certain 3beta-hydroxypregnane steroids are able to inhibit GABA's own effect. But that certain 3beta-hydroxy steroids would mainly inhibit GABA steroid effects on GABA gated chloride flux and other steroids would also inhibit GABA's own effect was not discovered or realized. This document does not mention the possibility to use 3beta-hydroxy-5alpha-pregnan-20-one against disorders caused by androgenic $GABA_A$ receptor modulation steroids and the possibility to use 3beta-hydroxy-5alpha-pregnan-20-one as inhibitor at the alpha4,beta,delta activated $GABA_A$ receptor and does not provide 3beta-hydroxy-5alpha-pregnan-20-one effects on phasic or tonic 3alpha-hydroxy-5alpha/beta-steroid activity in intra- or extra-synaptic receptors.

WO2008/063128 discloses the use of certain pregnane steroids in the treatment of CNS disorders. WO2008/063128 does not mention the possibility to use 3beta-hydroxy-5alpha-pregnan-20-one against disorders caused by androgenic $GABA_A$ receptor modulating steroids and the possibility to use 3beta-hydroxy-5alpha-pregnan-20-one as inhibitor at the alpha4,beta,delta activated $GABA_A$ receptor and does not provide 3beta-hydroxy-5alpha-pregnan-20-one effects on phasic or tonic 3alpha-hydroxy-5alpha/beta-steroid activity in intra- or extra-synaptic receptors.

It remains a challenge to find specific antagonists of the 3alpha-hydroxy-androstan/pregnane action on the $GABA_A$ receptor that have an activity on alpha4,beta,delta subtype and low inhibitory effects on GABA itself. In addition, it remains a challenge to find compounds that are physiologically safe and suitable for pharmaceutical use, and which additionally are applicable in physiologically acceptable doses with reasonable time intervals.

One objective of the present invention is thus to identify such specific blockers for $GABA_A$ receptor modulating steroid antagonism that are active against both 3alpha-hydroxy-androstan/androsten-steroids and 3alpha-hydroxy-pregnane/pregnene-steroids, and have effects on phasic and/or tonic 3alpha-hydroxy-5alpha/beta-steroid activity in intra- or extra-synaptic receptors, and especially on the alpha4,beta,delta subtype and to make available novel pharmaceuticals and methods for the treatment, alleviation or prevention of TS, OCD and/or GD.

Further objectives, the associated solutions and their advantages follow with the description, examples and claims.

DESCRIPTION OF THE INVENTION

The neuronal activity in the brain is decreased when the $GABA_A$ receptor is open and a large amount of chloride flux into the cell. It is also known that there is a relation between the amount of chloride moving in and the clinical effect of a $GABA_A$ receptor active drug. It is also known that $GABA_A$ receptors with different subunit composition reacts differently on 3alpha-hydroxy-delta 4-5, 5alpha/beta-steroids but there is no prior knowledge on how 3beta-hydroxy-5alpha-pregnan-20-one will act on different receptor subtypes e.g. alpha4,beta,delta receptor subtype or what effects 3beta-hydroxy-5alpha-pregnan-20-one will have on phasic or tonic 3alpha-hydroxy-5alpha/beta-steroid activity in intra- or extra-synaptic receptors or if 3beta-hydroxy-5alpha-pregnan-20-one can antagonize 3alpha-hydroxy, 5 alpha-androstane/androstene steroids.

3beta-hydroxy-5alpha-pregnan-20-one possesses a hydrogen donor in 3beta position, in the form of a hydroxy-group that surprisingly function as efficient blocker of the 3alpha-hydroxy-pregnan/pregnen-steroid action at the $GABA_A$ receptor subtype alpha1,beta,gamma but act differently on the alpha4,beta,delta subtype and can antagonize actions of 3alpha-hydroxy-androstane/androstene-steroids being positive $GABA_A$ receptor modulator. 3beta-hydroxy-5alpha-pregnan-20-one thus has utility as therapeutic substance for the prevention and/or treatment of Tourette's syndrome, obsessive compulsive disorder and/or gambling disorder and other related androgen/pregnen induced CNS disorders.

One aspect of the present invention is the therapeutic use of the above compound as blocking substances against the 3alpha-hydroxy-pregnan-steroid action on the alpha4,beta, delta $GABA_A$ receptor subtype and action on androgen metabolites active on the $GABA_A$ receptor. In addition, these substances are now suggested for the manufacture of pharmaceuticals for the treatment of Tourette's syndrome, obsessive compulsive disorder and/or gambling disorder or related steroid induced CNS disorders and for use in methods of treatment, according to the attached claims.

One aspect of the present invention relates to the effects 3beta-hydroxy-5alpha-pregnan-20-one have on phasic and tonic 3alpha-hydroxy-5alpha/beta-pregnan/pregnen-steroid activity or 3alpha-hydroxy-5alpha/beta-androstan/androsten-steroid activity in intra- or extra-synaptic receptors. 3beta-hydroxy-5alpha-pregnan-20-one thus has utility as therapeutic substance for the prevention and/or treatment of Tourette's syndrome, obsessive compulsive disorder and/or gambling disorder and other related androgen/pregnen induced CNS disorders.

The compound can be used alone or as prodrugs and/or in combination with formulations and other compositions in order to enhance and modulate the effects on CNS. Compositions within the scope of this invention include all compositions wherein the compound of this invention is contained in an amount that is effective to achieve the intended purposes.

The present inventors have identified that 3beta-hydroxy-5alpha-pregnan-20-one compound possesses a surprising function as efficient blocker of the 3alpha-hydroxy-androstane/pregnane action but is minimally active against GABA itself on the alpha4,beta,delta $GABA_A$ receptor subtype. 3beta-hydroxy-5alpha-pregnan-20-one has thus utility as therapeutic substance for the prevention and/or treatment of Tourette's syndrome, obsessive compulsive disorder and/or gambling disorder.

Before the present invention is further described, it is to be understood that the terminology employed herein is used for the purpose of describing particular embodiments only and is not intended to be limiting, since the scope of the present invention will be limited only by the appended claims and equivalents thereof.

In particular, it is noted that, as used in this specification and the appended claims, the singular forms "a", "an", and "the" also include plural referents unless the context clearly dictates otherwise.

The term "blocking" is meant to define an effect where in this case the 3alpha-hydroxy-5alpha/beta-steroids are prevented from acting on the $GABA_A$ receptor. It is understood that "blocking" is an entirely different effect than meant by "modulation" or "repression" or similar terms, which suggest that an action is still taking place, but to a lesser extent or at a slower rate.

The term "pharmaceutical composition" is used in its widest sense, encompassing all pharmaceutically applicable compositions containing at least one active substance, and optional carriers, adjuvants, constituents etc. The term "pharmaceutical composition" also encompasses a composition comprising the active substance in the form of derivate or a pro-drug, such as pharmaceutically acceptable salts, sulphates and esters. The manufacture of pharmaceutical compositions for different routes of administration falls within the capabilities of a person skilled in galenical chemistry.

The phrase "UC1010" denotes the compound 3beta-hydroxy-5alpha-pregnan-20-one.

The terms "administration" and "mode of administration" as well as "route of administration" are also used in their widest sense. The pharmaceutical composition of the present invention may be administered in a number of ways depending largely on whether a local, topical or systemic mode of administration is most appropriate for the condition be treated. These different modes of administration are for example topical (e.g., on the skin), local (including ophthalmic and to various mucous membranes such for example nasal, buccal, vaginal and rectal delivery), oral or parenteral and pulmonary, including the upper and lower airways.

The preparation of such compositions and formulations is generally known to those skilled in the pharmaceutical and formulation arts and may be applied to the formulation of the composition of the present invention.

The invention concerns 3beta-hydroxy-5alpha-pregnan-20-one, with surprising blocking effect of 3alpha-hydroxy-5alpha/beta-pregnan-20-one/ol, 3alpha-hydroxy-delta 4-5-pregnene-20-one/ol, on 3alpha-hydroxy-5alpha-androstan-17-ol/one and on 3alpha-hydroxy-delta 4-5-androsten-17-ol/one effects on the $GABA_A$ receptor subtype alpha4,beta,delta and thereby exerts a surprising therapeutic effect on Tourette's syndrome, obsessive compulsive disorder and/or gambling disorder and other 3alpha-hydroxy-delta 4-5,/5alpha/beta-steroid induced CNS disorders. The present invention arises out of the surprising finding that 3beta-hydroxy-5alpha-pregnan-20-one has an effect on the alpha4, beta,delta $GABA_A$ receptor subtype as an antagonist to positive modulators of the GABA receptor signaling.

The terms "steroid related" or "steroid induced" are meant to encompass the three possible mechanisms by which steroids act on the central nervous system: a) direct action, b) tolerance induction, and c) withdrawal effect. The present inventors have surprisingly identified that 3beta-hydroxy-5alpha-pregnan-20-one in pharmaceutically suitable and practically applicable doses can block the action of both 3alpha-hydroxy-pregnane and androstane steroids on the human $GABA_A$ receptor expressed in HEK-293 cells in vitro, thus blocking the development of the negative effects of 3alpha-hydroxy-pregnane and androstane steroids. In addition the present inventors have surprisingly shown that 3beta-hydroxy-5alpha-pregnan-20-one in pharmaceutically suitable and practically applicable doses can block the action of 3alpha-hydroxy-pregnane and androstane steroids on the human alpha4,beta,delta $GABA_A$ receptor subtype expressed in HEK-293 cells in vitro, thus blocking the development of the negative effects in CNS areas related to cortico-striato-thalamo-cortical circuits being the main $GABA_A$ receptor sub type involved in the pathogenesis of Tourette's syndrome, obsessive compulsive disorder and gambling disorder. Both the mechanism of action in Tourette's syndrome, obsessive compulsive disorder and gambling disorder by action of 3alpha-hydroxy-delta 4-5, 5alpha/beta-steroids particular androstane steroids, the mechanism of action on the alpha4,beta,delta subtype of $GABA_A$ receptor and the effect on phasic and tonic modulation of the $GABA_A$ receptor subtypes including alpha1 and alpha4 in pharmacological acceptable dosages have been addressed.

Figure 1:
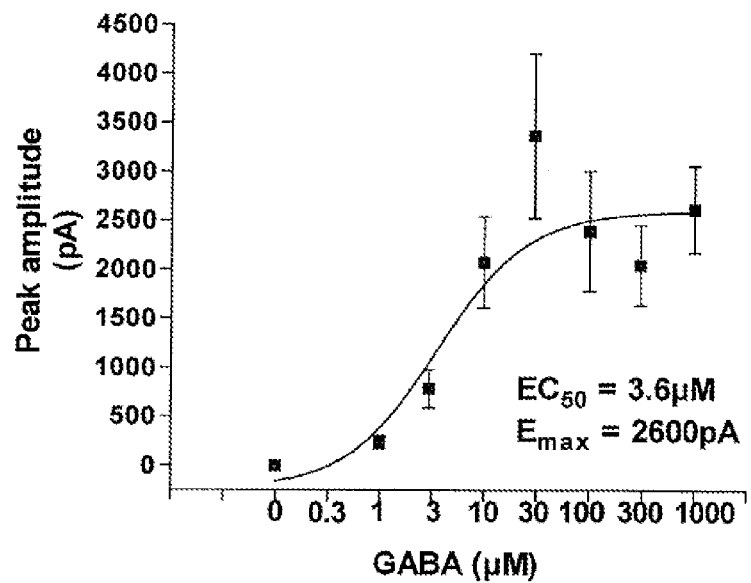
FIG. 1 shows that GABA increased the current response in a concentration-dependent way providing that the receptor alpha1,beta2,gamma2 had a normal and good response.

In one aspect of the invention, there is provided 3beta-hydroxy-5alpha-pregnan-20-one, for use in treatment of Tourette's syndrome, obsessive compulsive disorder and/or gambling disorder.

In one embodiment of this aspect, said disorder is Tourette's syndrome.

In one embodiment of this aspect, said disorder is obsessive compulsive disorder.

In one embodiment of this aspect, said disorder is gambling disorder.

In one embodiment of this aspect, said 3beta-hydroxy-5alpha-pregnan-20-one is provided in combination with at least one active compound, selected from serotonin reuptake inhibitors (SSRI), including citalopram, ecitalopram, fluoxetine, sertraline, and fluvoxamine; 5alpha-reductase blockers including finasteride or dutasteride; typical and atypical neuroleptics, including risperdone, ziprasidone, haloperidol, pimozide and fluphenazine; antihypertensive agents including clonidine, guanfacine, tricyclic antidepressants, clomipramine and opioid antagonists.

In one embodiment of this aspect, there is provided a pharmaceutical composition comprising 3beta-hydroxy-5alpha-pregnan-20-one, for said use, together with pharmaceutically acceptable carriers, excipients and/or diluents.

In one aspect of the invention, there is provided use of 3beta-hydroxy-5alpha-pregnan-20-one, in the preparation of a medicament useful in the treatment of Tourette's syndrome, obsessive compulsive disorder and/or gambling disorder.

In one embodiment of this aspect, said use is for treatment of Tourette's syndrome.

In one embodiment of this aspect, said use is for treatment of obsessive compulsive disorder.

In one embodiment of this aspect, said use is for treatment of gambling disorder.

In one embodiment of this aspect, said use of 3beta-hydroxy-5alpha-pregnan-20-one is provided in combination with at least one active compound, selected from serotonin reuptake inhibitors (SSRI), including citalopram, ecitalopram, fluoxetine, sertraline, and fluvoxamine; 5alpha-reducase blockers including finasteride or dutasteride; typical and atypical neuroleptics, including risperdone, ziprasidone, haloperidol, pimozide and fluphenazine; antihypertensive agents including clonidine, guanfacine, tricyclic antidepressants, clomipramine and opioid antagonists.

In one aspect of the invention, there is provided a method of treating, preventing or alleviating Tourette's syndrome, obsessive compulsive disorder and/or gambling disorder, comprising administering a pharmaceutically effective amount of 3beta-hydroxy-5alpha-pregnan-20-one, to a patient in need thereof.

In one embodiment of this aspect, said disorder is Tourette's syndrome.

In one embodiment of this aspect, said disorder is obsessive compulsive disorder.

In one embodiment of this aspect, said disorder is gambling disorder.

In one embodiment of this aspect, said 3beta-hydroxy-5alpha-pregnan-20-one is provided in combination with at least one active compound, selected from serotonin reuptake inhibitors (SSRI), including citalopram, ecitalopram, fluoxetine, sertraline, and fluvoxamine; 5alpha-reductase blockers including finasteride or dutasteride; typical and atypical neuroleptics, including risperdone, ziprasidone, haloperidol, pimozide and fluphenazine; antihypertensive agents including clonidine, guanfacine, tricyclic antidepressants, clomipramine and opioid antagonists.

The present invention concerns a method for the treating, preventing or alleviating Tourette's syndrome, obsessive compulsive disorder and/or gambling disorder in human patients described above, according to which method 3beta-hydroxy-5alpha-pregnan-20-one is administered to said patient. Suitable routes of administration are for example the following: intravenous, nasal, buccal, vaginal, rectal, subcutaneous, percutaneous and oral administration. Percutaneous administration, using the substances formulated as a cream, a gel, and an ointment or in the form of slow-release adhesive medicine patches, is another possible form of administration. In any of these or other routes of administration, the formulation of the composition may be adapted or adjusted according to normal pharmacological procedures, comprising the effective pharmaceutical in a chemical form, suitable for the chosen route, together with suitable adjuvants and vehicles, conventionally used and well-known to a person skilled in the art. Suitable, but not limiting, formulations for 3beta-hydroxy-5alpha-pregnan-20-one are provided in WO2011/087441.

Examples of symptoms and conditions caused by the action of 3alpha-hydroxy-5alpha/beta-steroids on the $GABA_A$ receptor are Tourette's syndrome, obsessive compulsive disorder and gambling disorder, tics frequency and type of presentation.

Exacerbation of Tourette symptoms (tics) caused by long time (days) exposure to 3alpha-hydroxy-5alpha/beta-steroids at stress, can according to the present invention, be prevented, alleviated or treated by the administration of 3beta-hydroxy-5alpha-pregnan-20-one to the patient.

One aspect of the invention, addressing a problem afflicting women with Tourette's syndrome, obsessive compulsive disorder and/or gambling disorder, is menstrual cycle linked increased frequency and/or change in tics type difficulties and a method for the treatment in human patients, according to which method 3beta-hydroxy-5alpha-pregnan-20-one is administered to said patient.

In general, the present invention encompasses the use of 3beta-hydroxy-5alpha-pregnan-20-one, either alone or in combination with other pharmaceuticals, such as serotonin reuptake inhibitors (SSRI), including citalopram, ecitalopram, fluoxetine, sertraline, and fluvoxamine; 5alpha-reductase blockers including finasteride or dutasteride; typical and atypical neuroleptics, including risperdone, ziprasidone, haloperidol, pimozide and fluphenazine; antihypertensive agents including clonidine, guanfacine, tricyclic antidepressants, clomipramine and opioid antagonists for the manufacture of a pharmaceutical for the treatment or prevention of any one of the 3alpha-hydroxy-delta 4-5, 5alpha/beta-steroid related or induced disorders described in the specification, and especially one or several of the following disorders: Tourette's syndrome, obsessive compulsive disorder and gambling disorder.

The invention will be described in the following, non-limiting examples.

Example 1

Assay for Testing $GABA_A$ Receptor Effects of 3Beta-Hydroxy-5Alpha-Pregnan-20-One on Human Alpha1,Beta, Gamma and Alpha4,Beta,Delta $GABA_A$ Receptor Subtype.

Aim:

To investigate the effect of 3beta-hydroxy-5alpha-pregnan-20-one on

1) $GABA_A$ receptor function in the absence and presence of GABA and 2) in absence and in presence of the positive $GABA_A$ receptor modulating steroids Tetrahydrodeoxycorticosterone (THDOC) and 3alpha-hydroxy-5alpha-androstan-17-ol (3alpha-OH-adiol) by the Dynaflow™ system on HEK-293 cells. In these tests the protocol was optimized to be similar to the physiological conditions in the synaptic cleft.

Cell Culture:

HEK-293 cells, permanently transfected with the human alpha1,beta,gamma and alpha4,beta,delta $GABA_A$ receptor subtypes, were seeded at a density of $3 \times 10^4/25$ $cm^2$ in cellbind culture flask. The transfected cells were used for patch-clamp experiments 3 days after seeding. When using the cells for patch-clamp experiments the cells were washed twice with oxygen-bubbled extracellular (EC) solution (see below). About 5 mL EC was then added and the cells were kept in the incubator for about 15 minutes. After 15 minutes the cells came loose from the bottom of the flask and were separated by carefully sucking couple of times with a Pasteur pipette.

Dynaflow™ system with Resolve chip was used for patch-clamp experiments: The electrophysiological recordings from HEK-293 cells were performed under voltage-clamp conditions using patch-clamp technique and the Dynaflow™ system (Dynaflow Pro II Platform Zeiss Axiovert 25; Cellectricon AB, Sweden) with Resolve chips as application system.

Patch pipettes were pulled from borosilicate glass and polished to a resistance 2-5 MΩ when filled with suitable intracellular solution (IC) (pH was adjusted to 7.2) and immersed in bath solution (extracellular, EC) (pH is adjusted to 7.4). The recordings were made using an Axopatch 200B amplifier, a Digidata 1322A (Axon instruments, Foster city, USA). Data were acquired using the pCLAMP software sampled at 10 kHz, filtered at 2-10 kHz and analyzed with Clampfit (versions 9.0, both from Axon instruments, Foster city, USA). No higher series resistance than 20 MΩ between pipette and cell membrane was accepted. No series resistance compensation was used. The stability of series resistance was monitored repeatedly from the time course of capacitative transients during the experiments. The measured liquid-junction potential between EC and IC was subtracted in all data presented. All experiments were performed at room temperature (21-23° C.).

Steroids and GABA:

GABA was dissolved in EC-solution by ultra sound for about 40 minutes to the concentration of 10 mM in room temperature. All steroids were dissolved to the concentration of 6 mM in DMSO. The DMSO concentration was 0.1% in all end-solutions, including the wash solution (EC) and the solution with GABA alone. End solutions were the solutions added into the wells of the chip.

Electrophysiology:

After compensating for the liquid junction potential a steady holding potential of −17 mV was used in all experiments. In physiological conditions the HEK-293 had a resting potential at −40 mV and a low concentration of chloride ions inside the cell. By using the holding potential of −17 mV and the intracellular solution with low chloride ion concentration the chloride ions flux into the cell when the receptors were activated.

Protocol

GABA Applications:

By using the Dynaflow equipment, it was possible to study transfected HEK-293 during almost physiological conditions. The Dynaflow system allowed application of solutions for as short as 40 ms up to minutes in time. Physiologically, in the synaptic cleft, GABA was released in mM range for about 2 ms. In these experiments we apply GABA±steroid for 40 ms. It was found that in almost all cells, the first GABA application gave a smaller response than the second GABA application. There was no difference in response between the second and the third GABA application. Therefore, the first GABA application was always repeated twice and the second response was used in the analysis.

Washout:

GABA is quite soluble in water and easy to washout from the receptor. The washout time was set to 1 minute after application with GABA solely. Steroids on the other hand were difficult to dissolve in water and also difficult to washout from the receptor. In the experiments, THDOC and 3alpha-OH-adiol were used as the positive $GABA_A$ receptor modulating steroids. With 2 minutes washout time, 200 nM THDOC and 3alpha-OH-adiol was completely washed out as shown by neither an accumulative nor a desensitization effect.

Incubation:

To see the effect of the steroids and to achieve stable results it was found that the steroids had to be incubated on the receptor before application of GABA. Different incubation times were studied to achieve the optimal time for attain stable results and minimize the washout time. Incubation time of 20 seconds showed to be the optimal time for washout time of 2 minutes.

Example 2

Biological Evaluation—HEK-293 Cells, Permanently Transfected with Human Alpha1,Beta,Gamma and Alpha4, Beta,Delta $GABA_A$ Receptor Subtypes and Expressing these $GABA_A$ Receptors.

Cell lines permanently expressing a functional human $GABA_A$ receptor was made in following steps. The $GABA_A$ receptor subunits alpha1, beta2 and gamma2L or alpha4, beta3 and delta including introduced Kozac sequences just before the start codons, were subcloned into mammalian expression vectors containing Geneticin, Hygromycin B, and Zeocin resistance, respectively. A HEK-293 cell line stably expressing the three $GABA_A$ receptor subunits was produced by transfection of the subunits one at a time. The transfection was followed by selection with the appropriate antibiotics, cell separation with the use of subunit specific antibodies, and production of single cell colonies. Produced cell lines were analysed with immunocytochemistry for the three $GABA_A$ receptor subunits, followed by selection of a suitable cell line showing for the $GABA_A$ receptor normal and good reactivity towards GABA, THDOC and 3alpha-OH-adiol. The $EC_{75}$ was calculated for THDOC and androstandiol and was used as enhancer of GABA when studying the effect of 1 µM 3beta-hydroxy-5alpha-pregnan-20-one.

Figure 2:
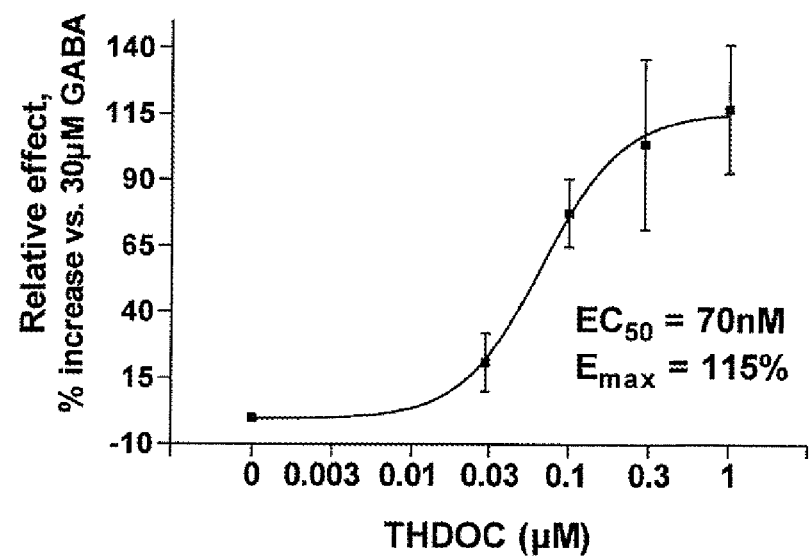
FIG. 2 shows that THDOC enhanced GABA mediated current response in a concentration-dependent way.

Results from tests of GABA in human $GABA_A$ receptor subtype alpha1, beta2, gamma2, permanently expressed in HEK-293 cells are presented in FIG. 1 and FIG. 2. FIG. 1 shows that GABA (1-1000 µM) increased the current response in a concentration-dependent way providing that the receptor alpha1,beta2,gamma2 had a normal and good response. FIG. 2 shows that THDOC (30-1000 nM)

enhanced GABA mediated current response in a concentration-dependent way. Control=30 µM GABA, was set to 0 (zero). The figure shows that the receptor alpha1,beta2, gamma2 had a normal and good response.

TABLE 1

THDOC alone significantly induced current response in absence of GABA at alpha4, beta3, delta receptor.

| THDOC (µM) Baseline shift | Mean ± SEM pA (N; P) |
|---|---|
| 0.03 | +5 ± 3.3 pA (N = 9; P = 0.008) |
| 0.1 | +15 ± 9.5 pA (N = 9; P = 0.003) |
| 0.3 | +12 ± 7.9 pA (N = 9; P = 0.019) |
| 1 | +69 ± 35 pA (N = 3; P = 0.018) |

Figure 3:
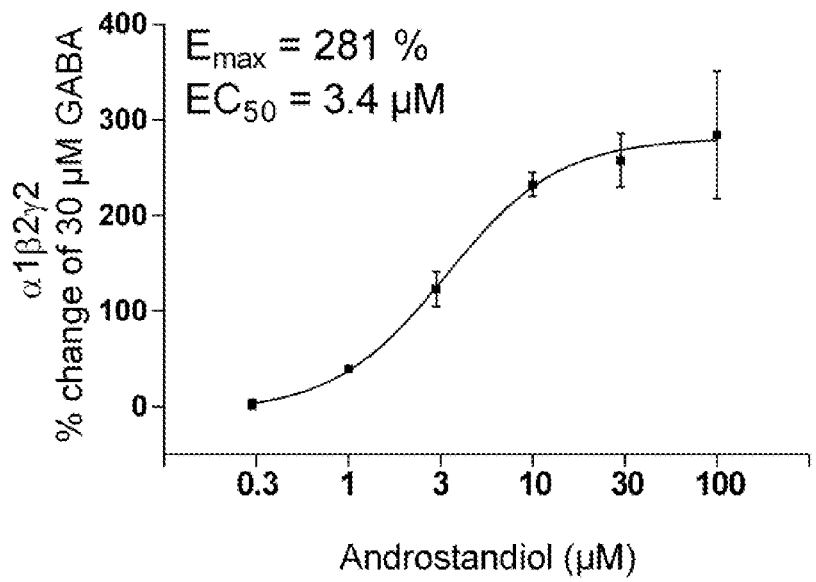
FIG. 3 shows that androstandiol enhanced 30 μM GABA mediated current response at alpha1,beta2,gamma2 human $GABA_A$ receptor sub type.

FIG. 3 shows that androstandiol (0.3-100 µM) enhanced 30 µM GABA mediated current response at alpha1,beta2, gamma2 human $GABA_A$ receptor sub type. The results in FIG. 3 show surprisingly that androstandiol was substantially less potent (48 times) than THDOC (FIG. 2) in enhancing the effect of GABA on the alpha1,beta2,gamma2 subunit receptor.

TABLE 2

Androstandiol (8-100 µM) induced current response in absence of GABA at alpha1, beta 2, gamma2 receptor.

| Androstandiol (µM) effect by itself (Baseline shift) | Mean ± SEM pA (N; P) |
|---|---|
| 3 | +8 ± 3.6 pA (N = 11; P = 0.004) |
| 8 | +13 ± 2.3 pA (N = 10; P = 0.005) |
| 10 | +11 ± 1.5 pA (N = 10; P = 0.000) |
| 30 | +24 ± 6.8 pA (N = 4; P = 0.001) |
| 100 | +43 ± 5.7 pA (N = 4; P = 0.001) |

Test of GABA in human GABA-A receptor subtype alpha4, beta3, delta permanently expressed in HEK-293 cells.

The recombinant human alpha4,beta3,delta $GABA_A$ receptor showed expected and normal concentration response curve to GABA (data not shown). Further, 1 µM 3beta-hydroxy-5alpha-pregnan-20-one GABA-mediated current response was without any significant effect on GABA alone at alpha4,beta3,delta $GABA_A$ receptor subtypes (data not shown).

Figure 4:
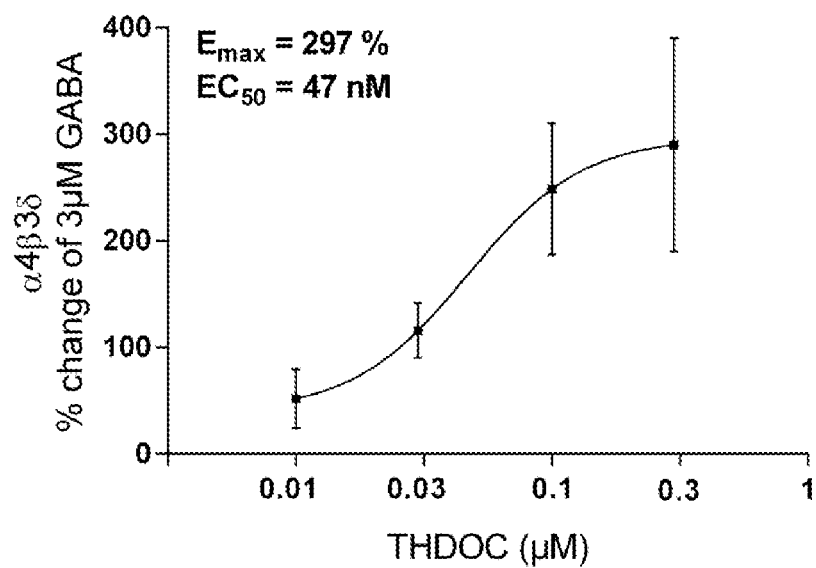
FIG. 4 shows that THDOC enhanced 3 μM GABA-mediated current in a concentration dependent way at alpha4,beta3,delta human $GABA_A$ receptor sub type.

FIG. 4 shows that THDOC (0.01-0.3 µM) enhanced 3 µM GABA-mediated current in a concentration dependent way at alpha4,beta3,delta receptor.

Figure 5:
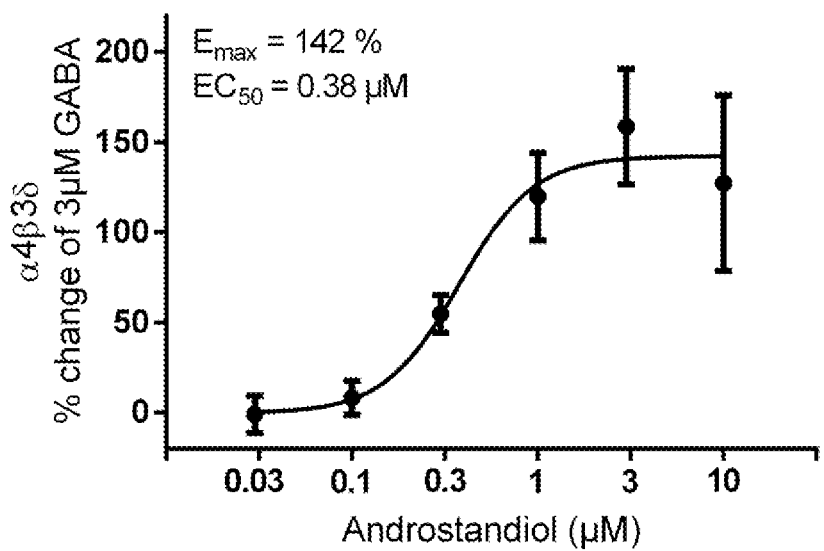
FIG. 5 shows that androstandiol enhanced 3 μM GABA-mediated current response at alpha4,beta3,delta human $GABA_A$ receptor sub type.

FIG. 5 shows that androstandiol (0.03-10 µM) enhanced 3 µM GABA-mediated current response at alpha4,beta3, delta receptor. The results are surprising since the potency of androstandiol in the alpha4,beta3,delta subunit composition was 10 times higher than in the alpha1,beta2,gamma2 subunit (FIG. 3: 0.38 µM vs. 3.4 µM).

Example 3

Experiments with Application of 3Beta-Hydroxy-5Alpha-Pregnan-20-One on the $GABA_A$ Receptor Subtype Alpha1, Beta2,Gamma2 and $GABA_A$ Receptor Subtype Alpha4, Beta,Delta.

Figure 6:
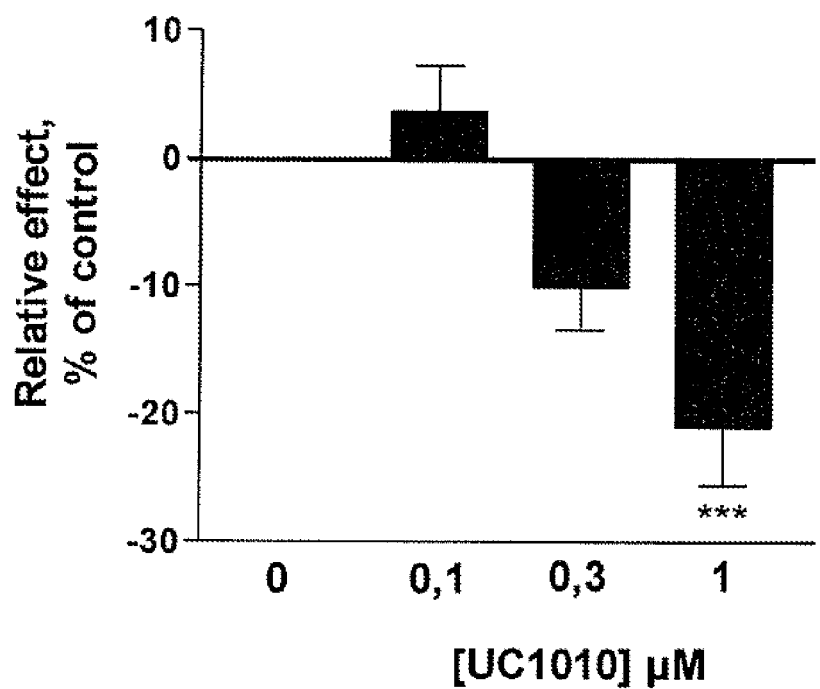
FIG. 6 shows that 3beta-hydroxy-5alpha-pregnan-20-one antagonized the THDOC effect.

Experiments with application on the $GABA_A$ receptor subtype alpha1,beta2,gamma2 showed (a) the inhibitory effect of 3beta-hydroxy-5alpha-pregnan-20-one on the effect of GABA+3alpha-hydroxy-5alpha-pregnan-21-one (THDOC) application at steady state (phasic effect), and (b) effect of 3beta-hydroxy-5alpha-pregnan-20-one on THDOC induced tonic effect (baseline shift). Steroid effect without GABA, steady state and steroid induced baseline shift (without THDOC and GABA), own effect of 3beta-hydroxy-5alpha-pregnan-20-one.

a) In the presence of 30 µM GABA+200 nM THDOC, a single dose of 1 µM 3beta-hydroxy-5alpha-pregnan-20-one antagonized the THDOC enhanced effect by −22.3±5.3% (p<0.001, n=6). In a separate concentration-dependent experiment, 3beta-hydroxy-5alpha-pregnan-20-one in the concentration interval 0.1-1 µM was tested in the presence of 200 nM THDOC and 30 µM GABA. FIG. 6 shows that 3beta-hydroxy-5alpha-pregnan-20-one antagonized the THDOC effect with max −21±4.6% (p<0.001; n=10) which was reached at 1 µM 3beta-hydroxy-5alpha-pregnan-20-one.

b) The modulatory effect of 1 µM 3beta-hydroxy-5alpha-pregnan-20-one in the presence of 30 µM GABA was positive but did not show any significant effect compared to GABA alone (+10.3±7.8%, NS, n=9, data not shown).

TABLE 3

Summary of the results at the receptor alpha1, beta2, gamma2.

| Test | $I_{max}/E_{max}$ | $IC_{50}/EC_{50}$ |
|---|---|---|
| 1-1000 µM GABA | 2600 pA | 3.6 µM |
| 0.03-1 µM THDOC + 30 µM GABA | +115% | 70 nM |
| 1 µM 3beta-hydroxy-5alpha-pregnan-20-one + 30 µM GABA | +10.3 ± 7.8% (N.S, n = 9) | — |
| 1 µM 3beta-hydroxy-5alpha-pregnan-20-one + 30 µM GABA + 200 nM THDOC | −21 ± 4.6% (P < 0.001, n = 10) | — |
| 0.1-1 µM 3beta-hydroxy-5alpha-pregnan-20-one + 30 µM GABA + 200 nM THDOC | −21% | 300 nM |

Table 4 shows application on a $GABA_A$ receptor subtype alpha4,beta,delta: a) GABA application, Steady state; b) the inhibitory effect of 3beta-hydroxy-5alpha-pregnan-20-one on the effect of GABA+3alpha-hydroxy-5alpha-pregnan-21-one (THDOC) application on a $GABA_A$ receptor subtype alpha4,beta,delta at steady state; c) effect on THDOC induced baseline shift, steroid effect without GABA. The THDOC induced baseline shift (without THDOC and GABA) is shown above in Table 1.

TABLE 4

Effect of 1 μM 3beta-hydroxy-5alpha-pregnan-
20-one on 3 μM GABA, on THDOC ± 3 μM GABA
at alpha4, beta3, delta receptor.

| The effect of 1 μM 3beta-hydroxy-5alpha-pregnan-20-one on | Mean ± SEM % (P; N) |
|---|---|
| a) Control 3 μM GABA response (%) | −6.7 ± 3.3% (N = 11, NS) |
| b) 0.1 μM THDOC + 3 μM GABA (%) | −26 ± 2.4% (N = 13, P = 0.001) |
| c) 0.1 μM THDOC alone baseline (%) | −43 ± 3.5% (N = 11, P = 0.003) |

Table 5 shows application on a GABA$_A$ receptor subtype alpha1,beta2,gamma2L: a) the inhibitory effect of 3beta-hydroxy-5alpha-pregnan-20-one on the effect of GABA+ 3alpha-hydroxy-5alpha-androstan-17-ol (3alpha-OH-adiol) application at steady state (phasic effect); b) effect on 3alpha-OH-adiol induced tonic effect (baseline shift); c) Androstandiol effect without GABA is shown in table 2.

TABLE 5

Effect of 1 μM 3beta-hydroxy-5alpha-pregnan-
20-one on 8 μM androstandiol ± 30
μM GABA at alpha1, beta2, gamma2.

| The effect of 1 μM 3beta-hydroxy-5alpha-pregnan-20-one on | Mean ± SEM % (P; N) |
|---|---|
| a) 8 μM Androstandiol + 30 μM GABA (%) | −30 ± 1.7% (N = 12, P = 0.001) |
| b) 8 μM Androstandiol, baseline shift (%) | −33 ± 7.6% (N = 8, P = 0.012) |

Maximal modulatory effect of 1 μM 3beta-hydroxy-5alpha-pregnan-20-one in presence of 30 μM GABA alone was not significant (10.3±7.8%, NS, n=9). This shows that 1 μM 3beta-hydroxy-5alpha-pregnan-20-one had no effect of GABA itself, therefore no further studies with 3beta-hydroxy-5alpha-pregnan-20-one and GABA alone was done.

Table 6 shows application on a GABA$_A$ receptor subtype alpha4,beta,delta: a) effect on 3alpha-OH-adiol induced baseline shift; b) the inhibitory effect of 3beta-hydroxy-5alpha-pregnan-20-one on the effect of GABA+3alpha-OH-adiol application on a GABA$_A$ receptor subtype alpha4,beta, delta at steady state; c) Androstandiol effect without GABA is shown below in table 7.

TABLE 6

Effect of 1 μM 3beta-hydroxy-5alpha-pregnan-
20-one on 3 μM GABA, on androstandiol ±
3 μM GABA and on THDOC + 3 μM GABA at alpha4, beta3, delta.

| The effect of 1 μM 3beta-hydroxy-5alpha-pregnan-20-one on | Mean ± SEM % (P; N) |
|---|---|
| a) 3 μM GABA response (%) | −6.7 ± 3.3% (N = 11, NS) |
| b) 0.6 μM Androstandiol + 3 μM GABA (%) | −18 ± 2.0% (N = 9, P = 0.008) |
| b) 0.8 μM Androstandiol + 3 μM GABA(%) | −22 ± 2.6% (N = 6, P = 0.028) |

TABLE 7

Androstandiol 3 μM and 10 μM significantly induce current
response in absence of GABA at alpha4, beta3, delta receptor.

| Androstandiol (μM) Baselineshift | Mean ± SEM pA (N; P) |
|---|---|
| 3 | +8 ± 3.6 pA (N = 11; P = 0.004) |
| 10 | +13 ± 4.8 pA (N = 12; P = 0.000) |

Androstandiol (3 μM and 10 μM) had a significant but minor effect on current response in absence of GABA compare to baseline, current response at EC-solution (Table 7). Androstandiol induced current response was so low that the effect of 1 μM UC1010 on the baseline shift was not possible to study.

Finally, 1 μM 3beta-hydroxy-5alpha-pregnan-20-one had no effect by itself at the alpha4,beta3,delta GABA$_A$ receptor by itself, −0.4±0.3 pA (N=11, NS) compare to current response at EC solution (−0.1±0.3 pA; N=10).

Hypothetical Example 1

There are several ways in which biological effects of treatment Tourette's syndrome, obsessive compulsive disorder and/or gambling disorder could be measured and confirmed. One non-limiting example is the transgenic mouse model described in Nordstrom & Burton 2002 (Nordstrom, E. J. & Burton, F. H. A transgenic model of comorbid Tourette's syndrome and obsessive-compulsive disorder circuitry. *Mol. Psychiatry* 7, 617-625, 524 (2002)), at least in relation to Tourette's syndrome. In brief, experiments are carried out as follow:

Animals

Male Balb/c mice with heterozygous D1CT-7 mutation (about 3 month-old) weighing approximately 20-30 g. Animals are purchased by Jackson Labs (Bar Harbor, Me.) and genotyped at arrival. Animals are housed in group cages with ad libitum access to food and water. The room is typically maintained at 22° C., on a 12 h: 12 h light/dark cycle from 8 am to 8 pm. Animals are tested during their light cycle between 12 and 4 pm to minimize any potential circadian effects.

Treatment

Treatment is with daily injections of 3beta-hydroxy-5alpha-pregnan-20-one subcutaneously (for instance, but not limited to, as a suspension in MCT oil) or placebo (the vehicle, e.g. MCT oil) in a randomized protocol.

Behavioral Studies

Tic-like manifestations are scored by trained observers blinded to the treatment, according to Nordstrom and Burton (2002). Tic-like manifestations are defined as rapid (<1 second) twitches of the head and/or body.

Statistical Analyses

Non-parametric statistics will be used. The significance threshold could be set at 0.05.

Collection of Blood Samples after 3Beta-Hydroxy-5Alpha-Pregnan-20-One Treatment

A separate set of animals not participating in the behavioral study is treated daily subcutaneously with 3beta-hydroxy-5alpha-pregnan-20-one in appropriate concentration for three days, and blood samples are taken at different time points, such as 2, 4, and 8 h, for determination of plasma concentration of 3beta-hydroxy-5alpha-pregnan-20-one.

CONCLUSIONS

The present invention thus surprisingly provides a possible treatment of Tourette's syndrome, obsessive compulsive disorder and gambling disorder as 3beta-hydroxy-5alpha-pregnan-20-one is active as a $GABA_A$ steroid modulator antagonist and thus can block the enhancement that the $GABA_A$ receptor modulating steroids induce in the main receptor subtypes located in thalamus of patients with Tourette's syndrome, obsessive compulsive disorder and gambling disorder.

1 µM 3beta-hydroxy-5alpha-pregnan-20-one acted as an antagonist to both androstandiol and to THDOC. 3beta-hydroxy-5alpha-pregnan-20-one significantly reduced the THDOC and androstandiol enhanced GABA mediated effect both at alpha1,beta2,gamma2 and at alpha4,beta3,delta $GABA_A$ receptor subtypes. Further, 1 µM 3beta-hydroxy-5alpha-pregnan-20-one significantly reduced the THDOC enhanced GABA mediated current response without any effect on GABA at alpha4,beta3,delta $GABA_A$ receptor subtype. 1 µM 3beta-hydroxy-5alpha-pregnan-20-one alone had no effect at the alpha4,beta3,delta $GABA_A$ receptor subtype.

Androstandiol enhanced the GABA mediated current response at both alpha1,beta2,gamma2 and alpha4,beta3,delta $GABA_A$ receptor subtypes. However, the $EC_{50}$ and $E_{max}$ differed between the subtypes. At the alpha1,beta2,gamma2 receptor the androstandiol $EC_{50}$ was 3.4 µM compared to 0.38 µM on alpha4,beta3,delta. Also, $E_{max}$ at the alpha1,beta2,gamma2 was 281% compared to Emax=142% at alpha4,beta3,delta. This provides that androstandiol was more efficient but less potent at the alpha1,beta2,gamma2 receptor compare to alpha4,beta3,delta receptor.

THDOC enhanced the GABA mediated current response at alpha4,beta3,delta $GABA_A$ receptor, where the $EC_{50}$ was 47 nM and $E_{max}$ was 297%. This provides that THDOC was more efficient and more potent at alpha4,beta3,delta $GABA_A$ receptor compared to androstandiol.

The invention claimed is:

1. A method of treating Tourette's syndrome, obsessive compulsive disorder and/or gambling disorder, comprising administering a pharmaceutically effective amount of 3beta-hydroxy-5alpha-pregnan-20-one, to a patient in need thereof.

2. The method according to claim 1, wherein the patient suffers from Tourette's syndrome, and 3beta-hydroxy-5alpha-pregnan-20-one is administered in an amount effective to treat the patient's Tourette's syndrome.

3. The method according to claim 1, wherein the patient suffers from obsessive compulsive disorder, and 3beta-hydroxy-5alpha-pregnan-20-one is administered in an amount effective to treat the patient's obsessive-compulsive disorder.

4. The method according to claim 1, wherein the patient suffers from gambling disorder, and 3beta-hydroxy-5alpha-pregnan-20-one is administered in an amount effective to treat the patient's gambling disorder.

5. The method according to claim 1, wherein 3beta-hydroxy-5alpha-pregnan-20-one is administered in combination with at least one additional active compound, selected from the group consisting of serotonin reuptake inhibitors (SSRI), 5alpha-reducase blockers, typical and atypical neuroleptics, antihypertensive agents, tricyclic antidepressants, and opioid antagonists.

6. The method according to claim 5 wherein the serotonin reuptake inhibitors (SSRI) are selected from the group consisting of citalopram, ecitalopram, fluoxetine, sertraline, and fluvoxamine.

7. The method according to claim 5 wherein the 5alpha-reducase blockers are selected from the group consisting of finasteride or dutasteride.

8. The method according to claim 1, wherein the 3beta-hydroxy-5alpha-pregnan-20-one is administered in a pharmaceutical composition comprising 3beta-hydroxy-5alpha-pregnan-20-one and one or more pharmaceutically acceptable carriers, excipients and/or diluents.

9. The method according to claim 5, wherein the typical and atypical neuroleptics are selected from the group consisting of risperdone, ziprasidone, haloperidol, pimozide and fluphenazine.

10. The method according to claim 5, wherein the antihypertensive agents are selected from the group consisting of clonidine and guanfacine.

11. The method according to claim 5, wherein the tricyclic antidepressant is clomipramine.

12. The method according to claim 1, wherein said 3beta-hydroxy-5-alpha-pregnan-20-one is administered intravenously, nasally, buccally, vaginally, rectally, subcutaneously, percutaneously or orally.

13. The method according to claim 1, wherein said 3beta-hydroxy-5-alpha-pregnan-20-one is administered topically, locally, orally, parenterally or pulmonary.

14. The method according to claim 1, wherein the 3beta-hydroxy-5-alpha-pregnan-20-one is in the form of a pharmaceutically acceptable salt, sulphate or ester.

* * * * *

UNITED STATES PATENT AND TRADEMARK OFFICE
CERTIFICATE OF CORRECTION

| | | |
|---|---|---|
| PATENT NO. | : 11,026,954 B2 | Page 1 of 1 |
| APPLICATION NO. | : 16/484940 | |
| DATED | : June 8, 2021 | |
| INVENTOR(S) | : Bäckström et al. | |

It is certified that error appears in the above-identified patent and that said Letters Patent is hereby corrected as shown below:

On the Title Page

Item (22) should be amended as follows:
PCT Filed: Feb. 9, 2018

Signed and Sealed this
Nineteenth Day of October, 2021

Drew Hirshfeld
*Performing the Functions and Duties of the*
*Under Secretary of Commerce for Intellectual Property and*
*Director of the United States Patent and Trademark Office*